US00PP28171P3

(12) United States Plant Patent
Byrne et al.

(10) Patent No.: US PP28,171 P3
(45) Date of Patent: Jul. 11, 2017

(54) NECTARINE TREE NAMED 'SMOOTH TEXAN ONE'

(50) Latin Name: *Prunus persica*
Varietal Denomination: SMOOTH TEXAN ONE

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 28 days.

(21) Appl. No.: 14/544,516

(22) Filed: Jan. 13, 2015

(65) Prior Publication Data

US 2016/0205828 P1 Jul. 14, 2016

(51) Int. Cl.
*A01H 5/08* (2006.01)

(52) U.S. Cl.
USPC ..... Plt./190

(58) Field of Classification Search
USPC ..... Plt./190
See application file for complete search history.

(56) References Cited

PUBLICATIONS

The Brooks and Olmo Register of Fruit and Nut Varieties, 3rd Ed., American Society of Horticultural Science Press, Alexandria, VA, 1997.
Anderson, P. C. and W. B. Sherman. 1995. 'Suncoast' nectarine. HortScience 30(2): 383-384.
Brooks, R. M. 1958. Double Delight, Earligold, and June Gold peaches. Fruit Var. J. 3:22.
Okie, W. R. 1998. Handbook of peach and nectarine varieties, USDA, ARS, Agric. Handbook No. 714.

*Primary Examiner* — Keith Robinson
(74) *Attorney, Agent, or Firm* — Ramey & Schwaller, LLP

(57) ABSTRACT

Disclosed is a new variety of *Prunus persica* named 'SMOOTH TEXAN ONE'. This new variety, which requires approximately 600 chilling units of dormancy, is considered to be a nectarine tree of early season maturity, ripening in mid- to late-May in the medium chill zone of Texas, which produces yellow fleshed fruit that are firm, attractively colored, and suitable for both local and regional markets.

4 Drawing Sheets

BACKGROUND OF THE INVENTION

Field of the Invention

This invention relates to nectarine trees and, more specifically, to nectarine trees referred to as a variety of *Prunus persica* named 'Smooth Texan One'. 'SMOOTH TEXAN ONE', which requires approximately 600 chilling units of dormancy, produces a high quality, firm, yellow-fleshed clingstone nectarine that matures early in the season.

SUMMARY OF THE INVENTION

The "SMOOTH TEXAN ONE' nectarine is characterized as to novelty and is otherwise noteworthy by producing yellow-fleshy nectarine fruit that ripens in the early season; is considered high quality; and which is firm and has an attractive red skin coloration. In this regard, the present variety of nectarine tree bears fruit that are ripe for commercial harvesting and shipment about mid- to late-May, when the fruit is grown in the medium chill zone of Texas. "SMOOTH TEXAN ONE' ripens about 2 weeks before the 'June Gold' peach, (U.S. Plant Pat. No. 1,884). Additionally, the new variety exhibits the potential to be commercialized in regions that have chilling requirements that are relatively low.

Origin of the Variety

The present nectarine tree was the result of an ongoing Stone Fruit Breeding Program of Texas A & M University, College Station, Brazos County, Tex. To this end, controlled crosses are made each year to produce seedling populations from which improved progenies are evaluated and selected.

The seedling "SMOOTH TEXAN ONE' originated at the Texas A & M University Horticultural Farm in College Station, Tex. in 2005. It was chosen from a population of seedlings that resulted from seed from a cross between 'Crimson Baby' (not patented, Okie, 1998), a yellow fleshed, medium chill nectarine released by the USDA Stone Fruit Breeding Program in Fresno, Calif. (Okie, 1998) as the female parent and a low chill nectarine selection (TX2C104N, unreleased, not patented) derived from an open pollinated progeny of 'Suncoast' (not patented, Andersen and Sherman, 1995) as the male (pollen) parent. 'Crimson Baby' is a cross between the University of Florida nectarine selection G69-83 [(Okinawa×Panamint)×Sunrise] as a female parent and 'Mayfire' nectarine (not patented, Ramming and Tanner, 1987) as the male parent. 'Suncoast' is a yellow fleshed, low chill nectarine released by the Stone Fruit Breeding Program at the University of Florida. The complex pedigree of 'Suncoast' includes 'Sungold' (not patented), 'Armking' (U.S. Plant Pat. No. 2,943), 'Sunred' (not patented), 'Sunrich' (not patented), 'Southland' (not patented), 'Jewel' (not patented), 'Panamint' (not patented), and 'Hawaiian' (not patented, Anderson and Sherman, 1995). Resulting seed from this cross were planted in 2003 at the Texas A & M University Horticultural Farm in College Station, Tex. The seedling 'Smooth Texan One'

(TX3B298N) was marked for subsequent observation and noted as having exceptional characteristics. Two-year and older trees of the variety were subsequently evaluated during the 2007 through 2011 fruit growing seasons in both California (Clovis) and Texas (Fairfield, Terrell and College Station).

Asexual Reproduction of the Variety

'SMOOTH TEXAN ONE' was bud grafted onto virus-free Nemaguard (not patented, Brooks and Olmo, 1997) peach rootstock in June 2005 at the nursery site in Oakdale, Calif. The variety was subsequently planted at the experimental orchard in the central portion of the San Joaquin Valley, near Fowler, Fresno County, Calif. and in three sites in Texas (College Station, Fairfield and Terrell). Fruit from the resulting propagation has been evaluated during the period from 2007-2011 fruiting seasons. This evaluation clearly demonstrated that the re-propagated trees were true to the characteristics of the original seedling in all observable aspects.

BRIEF DESCRIPTION OF THE DRAWINGS

This new variety of nectarine tree is illustrated by the accompanying photographs. The fruit, pits, flowers, and shoots depicted are from mature trees that are 5-years of age.

BOTANICAL DESCRIPTION OF THE VARIETY

Figure 1:
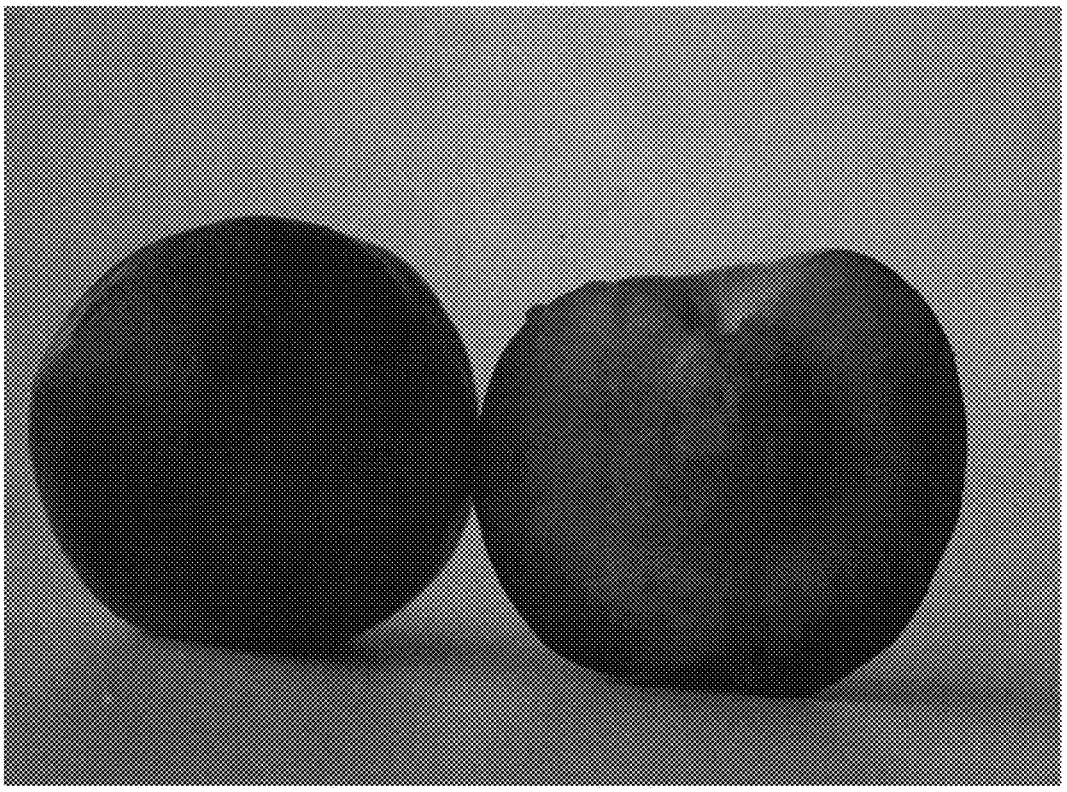
FIG. 1. Color picture showing the flesh and skin color and fruit shape of 'Smooth Texan One' produced in the medium chill zone of Texas (Fairfield).
Figure 2:
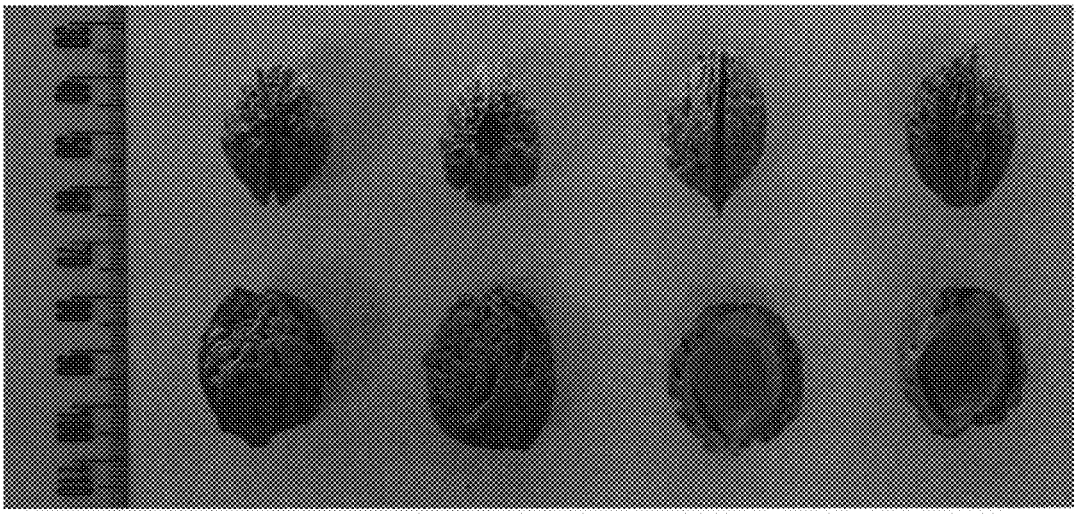
FIG. 2. Color photograph of the endocarp of 'Smooth Texan One'. The ruler is demarcated in millimeters.
Figure 3:
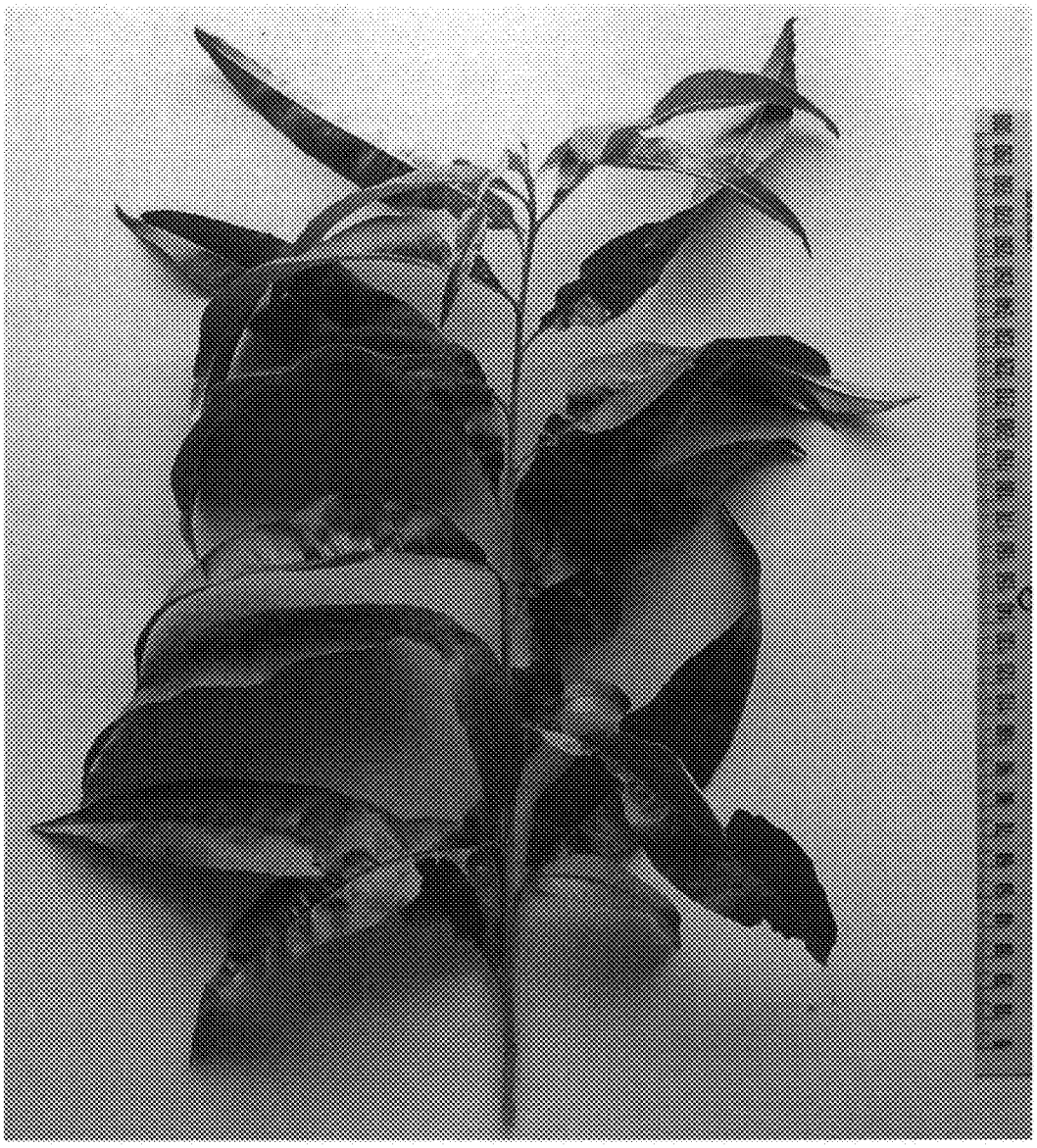
FIG. 3. A stem showing the leaves of the 'Smooth Texan One' nectarine. The ruler is demarcated in millimeters.
Figure 4:
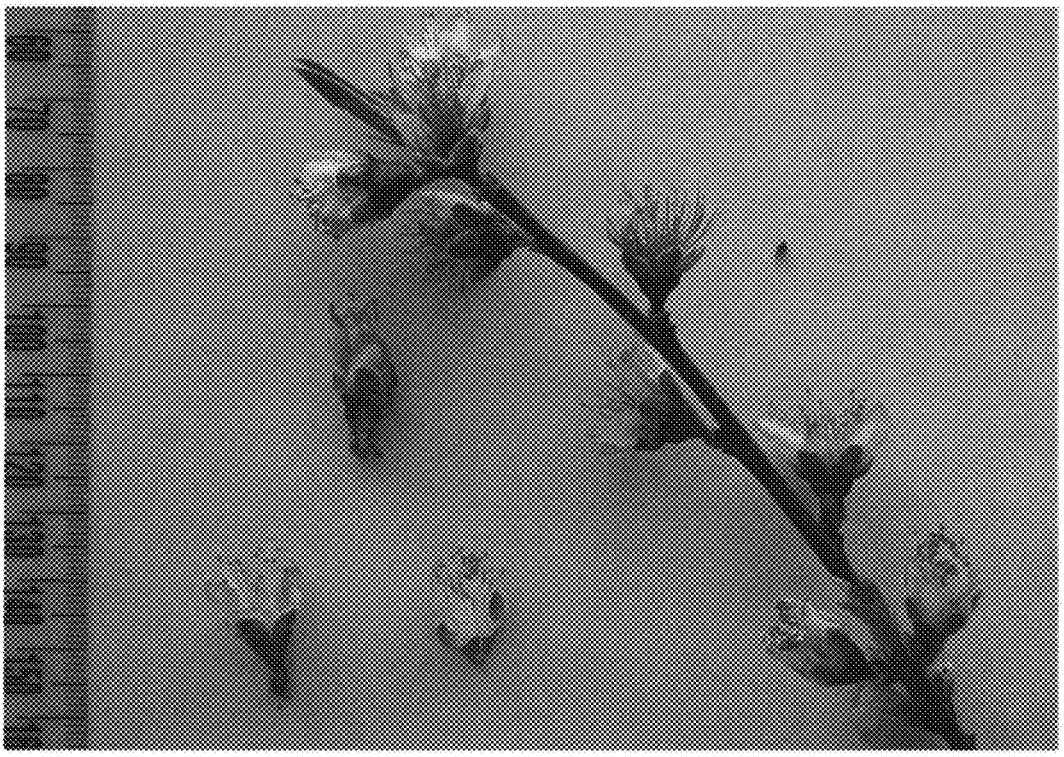
FIG. 4. The non-showy flowers of 'Smooth Texan One'. The ruler is in millimeters.

Referring more specifically to the pomological details of this new and distinct variety of nectarine tree, the following has been observed under the ecological conditions prevailing at the experimental orchards in medium chill zone of Texas on mature five-year old trees. All major color code designations are by reference to The R.H.S. Colour Chart (2001) provided by The Royal Horticultural Society of Great Britain. Colors are approximate as color depends on horticultural practices such as light level and fertilization rate, among others.

Tree

Size: Generally average to above average as compared to other common peach and nectarine cultivars ripening in the early season of maturity.

Height: 7 feet (2.13 m) at the end of the 2012 growing season on a five-year old tree.

Width: 3 feet (0.91 m) at the end of the 2012 growing season on a five-year old tree.

Vigor: High.

Density: Medium to high.

Productivity: Productive.

Shape: The trees are vigorous with the typical semi-spreading growth habit similar to 'TexKing' (U.S. Plant Pat. No. 14,627), 'TexPrince' (U.S. Plant Pat. No. 14,629), and 'TexRoyal' (not patented, Byrne and Bacon, 1991).

Current season growth: The current season growth for the new variety was approximately 3.1 to 4.5 feet (0.94-1.37 m).

Regularity of bearing: Regular, and considered hardy under typical climatic conditions found in the medium chill zone of Texas and in the central San Joaquin Valley, Calif.

Trunk

Size: Approximately 3.0 inches (7.62 cm) in diameter and 10.5 inches (26.67 cm) in circumference when measured at a distance of approximately 12 inches (30.5 cm) above the soil level, at the end of the 2012 growing season on a five-year old tree.

Bark texture: Considered moderately rough with numerous folds of papery scarf-like skin being present.

Bark coloration: Variable, colors present are 166A of the Greyed-Orange Group, 183A-B of the Greyed-Purple Group, 198D of the Greyed-Green Group and 202D of the Black Group.

Branches

Size: Considered medium to large for the variety. The length of the branches are limited by pruning to a 3 to 5 foot (approximately 0.9 to 1.5 m) length depending on its position in the tree.

Thickness: Average (about 4.0 cm in diameter as measured 10 cm from the trunk on a five-year old tree) as compared to other varieties.

Surface texture: Average and appearing furrowed on wood that is several years old.

Lenticels: Numerous flat, oval lenticels present. The lenticels range in size from approximately 1 to 4 mm in width and were approximately 1 mm in height.

Current season shoots: Surface texture—Substantially glabrous.

Internode length: Approximately 3 to 5 cm as measured in the middle of a current season stem.

Color of mature branches: The predominant colors are 174A, 175A-B and 176A-C of the Greyed-Orange Group, 198D of the Greyed-Green Group and N200D of the Brown Group.

Current season shoot: Color—Light green (139D and 142C-D of the Green Group) with some reddish-brown coloration appearing on exposed surface of the shoots (166C-D of the Greyed-Orange Group). The upper exposed surface of the current season growth exhibits weak to medium intensity of anthocyanins. The color of new shoot tips is considered a bright and shiny green (mainly 142C-D of the Green Group).

Leaves

Size: Considered medium sized for the species. Leaf measurements have been taken from vigorous upright current season growth approximately at mid-shoot.

Leaf length: Approximately 145 to 165 mm.

Leaf width: Approximately 38 to 43 mm.

Leaf thickness: Less than 1 mm.

Leaf form: Lanceolate.

Leaf tip form: Acuminate.

Leaf upper surface color: Green, varying among 137B and 147A of the Green and Yellow-Green Groups respectively.

Leaf lower surface color: Green, approximately 146A-B of the Yellow-Green Group.

Leaf mid-vein color: Light green, varying among 145C and 154D of the Yellow-Green Group.

Leaf margins:

*Form*.—Considered crenate/crenulate.

*Uniformity*.—Considered generally uniform.

Leaf petioles:

*Size*.—Considered medium long.

*Length*.—Approximately 9 to 12 mm.

*Thickness*.—Approximately 1.5 to 2 mm.

*Color*.—Pale green (145C and 154D of the Yellow-Green Group).

Leaf glands:

*Size*.—Approximately 1-3 mm in height and 1-2 mm in width.

*Number*.—Generally 2-4 per leaf.

*Type*.—Reniform.

*Color*.—Light brown (165B of the Greyed-Orange Group and N199A of the Grey-Brown Group).

Leaf stipules:

*Size*.—Medium size for the species.

*Length*.—Approximately 10 to 12 mm.

*Width*.—Generally less than 1 mm.

*Form*.—Lanceolate.

*Color*.—Light green (143D of the Green Group) with reddish brown tips (177C-D of the Greyed-Orange Group) when young. The stipules are considered to be early deciduous.

*Ratio of wood (leaf) buds to flowering buds*.—1 to 2 flower buds per vegetative bud.

Flowers

Floral buds:

*General*.—The floral buds are considered to be medium to medium large in size, conic in form, and slightly appressed relative to the bearing shoot.

*Color*.—The bud scales are brown-orange, (approximately Greyed-Orange Groups 165A and 166A and the Brown Group 200B-C). The buds are considered hardy under the typical climatic conditions found in the medium chill zone of Texas and in the central San Joaquin Valley, California.

*Length*.—Approximately 5 to 6 mm.

*Width*.—Approximately 1.5-2.5 mm.

*Blooming type*.—Considered medium early in relation to other peach and nectarine cultivars commonly growing in the medium chill zone of Texas. Date of full bloom was between March 1st and March 10th during the period between 2007 and 2011. Mean bloom date was March 6th which is about 3 days before 'June Gold' (U.S. Plant Pat. No. 1,884).

*Flower type*.—Non-showy.

*Flower size*.—Flower diameter at full bloom is approximately 16 to 24 mm. The length of the flower at the pink bud stage before opening is approximately 15 mm.

*Bloom quantity*.—Considered abundant.

*Flower bud frequency*.—Normally 1 to 2 per node.

Petal size:

*General*.—Considered medium small for the species.

*Width*.—Approximately 6 to 7 mm.

*Length*.—Approximately 12 mm.

*Petal form*.—Ovate.

*Petal count*.—Nearly always 5.

*Petal color*.—Medium pink when young (Red-Purple Group 62B-C, 63D and 65A), becoming lighter near the petal claw.

Petal claw:

*Form*.—The claw is considered truncate in shape and has a medium size when compared to other varieties.

*Length*.—Approximately 1 mm.

*Width*.—Approximately 1 mm.

*Petal margins*.—Generally considered variable, from nearly smooth to slightly undulate.

*Petal apex*.—Generally — The petal apices appear slightly domed.

Flower pedicel:

*Length*.—Considered short, and having an average length of approximately 2 to 3 mm.

*Thickness*.—Considered average, approximately 1 mm.

*Color*.—A light green with dark maroon (Yellow-Green Group N144B-D, 144B-D, 145A-B, Greyed-Red 178A-B, Greyed-Purple 183A-C, 184A-B and 187C).

Floral nectaries:

*Color*.—Medium orange (Orange Group 24A, 25A-B, N25A-B and 26A).

Calyx:

*Surface texture*.—Generally glabrous.

*Color*.—Maroon (Greyed-Red Group 178A-B, 181A, Greyed-Purple Group 183A-C, 184A-B, 185A-B and 187C).

Sepals:

*Surface texture*.—The surface has a short, fine, and wooly texture.

*Size*.—Average, and ovate in form. The sepals vary in length from 5.0 mm to 5.4 mm and in width from 4.2 mm to 4.8 mm.

*Color*.—A dull maroon (Greyed-Red Group 178A-B, Greyed-Purple Group 183A-C and 185A).

Anthers:

*General*.—Average in size for the species. The anthers are approximately 1.5 mm in length and 0.7-1.1 mm in width.

*Color*.—Golden yellow with dark orange when young (Yellow Group 6A-B, 7A-B, 12A-C, 13B-C, Orange Group N25A-B and 28A-B) and becoming darker with advanced senescence.

*Pollen production*.—Pollen is abundant, and is a yellow color (approximately Yellow Groups 5A-B and 12A-13B).

Filaments:

*Size*.—Variable in length, approximately 13 to 15 mm, with the filaments equal to or slightly shorter than the pistil. The stamens are generally equal or slightly below the pistil and protrude when the flowers are at the later stages of the pink bud stage of development.

*Color*.—White when young (approximately White Group 155A-D) and darkening to light pink (Red-Purple Group 62B-D, 63D, 65b-D, 68D and 69A) with advanced maturity.

Pistil:

*General*.—Average in size, but equal to or slightly longer than the general anther height.

*Length*.—Approximately 14 to 17 mm, including the ovary.

*Color*.—Considered a very light yellow-green when young (Green-Yellow Group 1A-D), with a red color developing near the stigma (Red Group 45A-B and 46A-B).

*Surface texture*.—Pubescence absent. The pistil including the ovary is not pubescent.

Fruit

Maturity when described: The present variety of fruit is described, as it would be found in its firm ripe condition at full commercial maturity. Under the ecological conditions prevailing in the medium chill zone of Texas 'Smooth Texan One' ripens in mid to late May, a week before 'Regal' (not patented, Johnson et al., 1994) and about 2 weeks before 'June Gold' (U.S. Plant Pat. No. 1,884).

Size: General—Medium large for the season and considered uniform.

Average cheek diameter: Approximately 56 to 65 mm.

Average suture diameter: Approximately 54 to 70 mm.

Average axial diameter: Approximately 55 to 64 mm.

Fruit form: Generally round to slightly ovate in its lateral aspect.

Fruit suture: Generally, the suture appears as a thin line that extends from the base to the apex, and appears deeper at the apex, forming a shallow basin at the apical point. No apparent callusing or stitching exists along the suture line.

*Color*.—Dark red (Orange-Red Group N34A and Red Group 46A-C).

*Ventral surface*.—Form — Considered uniform.

Stem cavity:

*Size*.—Considered moderately shallow for the species.

*Length*.—Approximately 22 to 30 mm.

*Width*.—Approximately 13 to 18 mm.

*Depth*.—Approximately 9 to 14 mm.

*Fruit base*.—Generally considered flat and tapering.

*Fruit apex*.—Generally considered flat and round.

Fruit stem:

*Length*.—Approximately 8 to 12 mm.

*Thickness*.—Approximately 3 to 5 mm.

*Color*.—Generally a medium brown with green (Yellow-Green Groups 144A-C and 154B and Greyed-Orange Group 166A-B).

Fruit skin: Generally considered medium or average in thickness.

*Surface texture*.—Smooth.

*Skin acidity*.—Considered neutral to slightly acid.

*Tenacious to flesh*.—Yes at commercial maturity.

*Tendency to crack*.—Not observed.

*Skin color*.—Generally — Variable, with a high (70%) to very high (90%) percentage of the fruit surface covered with blush as described under Blush Color below.

*Pubescence*.—Absent. The glabrous skin has a medium glossiness.

*Blush color*.—This blush ranges from a dark maroon (Red-Purple Group 59A-B) to medium red (Red Group 43A-C) with many degrees of shading and blending occurring between these colorations.

*Skin ground color*.—Dark Yellow (Yellow-Green Group 1A-B and Yellow Group 7A).

*Flesh color*.—Medium Yellow (Yellow Groups 3A, 5A and 6A-B) with a red color appearing near the skin (Orange-Red Group 30A-B).

*Flesh fibers*.—Fibers are present in the flesh.

*Stone cavity color*.—Medium to light yellow (Yellow Groups 4D and 6A-B).

*Flesh texture*.—Generally, the flesh is considered medium firm and fine at commercial maturity.

*Ripening*.—Generally the fruit of the present variety ripens evenly.

*Flavor*.—Considered sweet with a slightly acidic flavor.

*Aroma*.—Pleasant and reasonably abundant.

*Eating*.—Generally considered very good for an early ripening variety.

Stone

Attachment: Clingstone (strongly adherent) at commercial maturity.

Stone size: Generally considered medium-large to large relative to the ratio of stone to fruit size.

*Length*.—Approximately 36 to 39 mm.

*Width*.—Approximately 29 to 30 mm.

*Thickness*.—Approximately 19 to 21 mm.

*Fibers*.—Generally a few medium length fibers are attached along the entire surface of the stone.

*Stone form*.—Generally variable, from rounded to elliptical.

*Stone base angle*.—Medium.

*Apex shape*.—Narrow.

*Stone shape*.—Considered variable, from rounded to ovid.

Stone surface:

*Surface texture*.—Minor surface markings are honeycombed with pit grooves.

*Ridges*.—Few ridges are present basally.

*Ventral edge*.—Small.

*Dorsal edge*.—Shape — Grooved and having moderately rough edges.

*Stone color*.—The color of the dry stone is light brown (161B-C of the Greyed-Yellow Group, and 164C-D and 165D of the Greyed-Orange Group). The color of the inside surface of the endocarp is primarily 158A of the Yellow-White Group, 159B of the Orange-White Group, 161D of the Greyed-Yellow Group and 164D of the Greyed-Orange Group.

*Tendency to split*.—Splitting is relatively uncommon.

*Kernel*.—The kernel fills the endocarp at harvest and measures approximately 4-6 mm in thickness, 10-12 mm in width, and 16-19 mm in length. When dried the shriveled kernels measure approximately 2-3 mm in thickness, 9-10 mm in width, and 14-16 mm in length. The colors of the shriveled kernels are primarily 165A, 167A and 177A of the Greyed-Orange Group, N199B-C of the Grey-Brown Group and 200D of the Brown Group.

Use: The subject variety, 'SMOOTH TEXAN ONE', is considered to be a nectarine tree of early-season maturity, which produces yellow-fleshed fruit which are firm, attractively colored, and which are useful for both local and long distance shipping.

Keeping quality: Good.

Resistance to insects and disease: No particular susceptibilities or resistances were noted or are claimed.

Shipping quality: Average.

Although the new variety of nectarine tree possesses the described characteristics when grown under the ecological conditions prevailing in the medium chill zone of Texas, it will be understood that variations of the usual magnitude and characteristics incident to the changes in growing conditions, fertilization, pruning, and pest control are to be expected.

REFERENCES

Anderson, P. C. and W. B. Sherman. 1995. 'Suncoast' nectarine. HortScience 30(2): 383-384.

Anon. 2001. R.H.S. Colour Chart. The Royal Hort. Soc., London.

Brooks, R. M. 1958. Double Delight, Earligold, and June Gold peaches. Fruit Var. J. 3:22, U.S. Plant Pat. No. 1,884.

Byrne, D. H. and T. A. Bacon. 1991. 'TexRoyal', a medium chilling peach. HortScience 26(10):1338-1340.

Byrne, D. H. and T. A. Bacon. 2004. 'TexKing', an early ripening medium chill peach. HortScience 39: 442-443. U.S. Plant Pat. No. 14,627. Mar. 23, 2004.

Byrne, D. H. and T. A. Bacon. 2004. 'Texprince', a mid season, medium chill peach. HortScience 39(3):631-632. U.S. Plant Pat. No. 14,629. Mar. 23, 2004.

Johnson, C. E., J. T. Payne, W. A. Young, and E. W. Bush. 1994. Regal peach. HortScience 29:1094.

Okie, W. R. 1998. Handbook of peach and nectarine varieties, USDA, ARS, Agric. Handbook No. 714.

Ramming, D. W. and O. Tanner. 1987. 'Mayfire' nectarine. Fruit Var. J. 41(2):80-81.

We claim:

1. A new and distinct *Prunus persica* tree, substantially as illustrated and described herein.

* * * * *